United States Patent
Soubelet et al.

(10) Patent No.: US 8,467,850 B2
(45) Date of Patent: Jun. 18, 2013

(54) SYSTEM AND METHOD TO DETERMINE THE POSITION OF A MEDICAL INSTRUMENT

(75) Inventors: Elisabeth Soubelet, New Delhi (IN); Regis Vaillant, Buc (FR)

(73) Assignee: General Electric Company, Schenectady, NY (US)

( * ) Notice: Subject to any disclaimer, the term of this patent is extended or adjusted under 35 U.S.C. 154(b) by 189 days.

(21) Appl. No.: 12/754,693

(22) Filed: Apr. 6, 2010

(65) Prior Publication Data

US 2010/0261999 A1    Oct. 14, 2010

(30) Foreign Application Priority Data

Apr. 8, 2009    (FR) ................................ 09 52298

(51) Int. Cl.
*A61B 6/00*    (2006.01)

(52) U.S. Cl.
USPC ............................................ 600/424

(58) Field of Classification Search
USPC ................................ 600/407, 424, 425
See application file for complete search history.

(56) References Cited

U.S. PATENT DOCUMENTS

| 4,737,921 | A | 4/1988 | Goldwasser et al. | |
| 2003/0074011 | A1* | 4/2003 | Gilboa et al. | 606/130 |
| 2005/0033142 | A1 | 2/2005 | Madden et al. | |
| 2008/0137924 | A1 | 6/2008 | Boese et al. | |
| 2008/0177280 | A1 | 7/2008 | Adler et al. | |
| 2008/0228068 | A1 | 9/2008 | Viswanathan et al. | |
| 2008/0262342 | A1* | 10/2008 | Averbruch | 600/424 |
| 2008/0273784 | A1 | 11/2008 | Pfister | |
| 2009/0076476 | A1* | 3/2009 | Barbagli et al. | 604/500 |
| 2009/0148009 | A1 | 6/2009 | Mielekamp et al. | |
| 2010/0020160 | A1 | 1/2010 | Ashbey | |

FOREIGN PATENT DOCUMENTS

| EP | 2048617 A2 | 4/2009 |
| WO | 2006056909 A1 | 6/2006 |
| WO | 2009023801 A1 | 2/2009 |

OTHER PUBLICATIONS

Florence Grassi et al., Jun. 10, 2010, U.S. Appl. No. 12/813,092.
French Search Report and Written Opinion from FR Application No. 0953952, dated Feb. 4, 2010.
Non-Final Rejection from U.S. Appl. No. 12/813,092 Dated Aug. 16, 2012.

* cited by examiner

*Primary Examiner* — Jacqueline Cheng
(74) *Attorney, Agent, or Firm* — Global Patent Operation

(57) ABSTRACT

A medical imaging method for the navigation of a guidable medical instrument intended to be moved inside the body of a patient, comprising: receiving at least one 2D image of a cavity of a patient, acquired by an acquisition device, for which cavity a 3D representation is available; receiving at least one data item on the force applied to the medical instrument to control a guiding of the medical instrument inside the patient's body; and combining data derived from information on applied force, the 2D image and the 3D representation to determine the position of the medical instrument.

6 Claims, 2 Drawing Sheets

SYSTEM AND METHOD TO DETERMINE THE POSITION OF A MEDICAL INSTRUMENT

CROSS-REFERENCE TO RELATED APPLICATION

This application claims priority under 35 U.S.C. §119(a)-(d) or (f) to prior-filed, co-pending French application number 0952298, filed on Apr. 8, 2009, which is hereby incorporated by reference in its entirety.

BACKGROUND OF THE INVENTION

1. Field of Invention

The present invention generally concerns the area of interventional radiology.

More particularly, the present invention relates to imaging methods and systems to determine the position of a medical instrument positioned inside a patient.

2. Description of Related Art

The principle of interventional radiology procedures, for a user, consists of guiding and deploying a medical instrument inside a patient, being assisted by a medical imaging system.

This medical imaging system allows real-time acquisition, processing and display of data on the position of the instrument, and a gives a representative image of inside the patient.

Medical imaging systems have already been proposed allowing the display of a three-dimensional (3D) illustration of a medical instrument in its current position and of the patient's vascular system.

Document U.S. Pat. No. 6,317,621 describes a medical imaging system comprising acquisition means, processing means and display means. The display means allow the display of a 3D representation illustrating the medical instrument in its current position and the patient's vascular system. To calculate the 3D position of the medical instrument, the processing means use two 2D images acquired simultaneously at different angles by the acquisition means.

However, the simultaneous acquisition of two 2D images requires the emission of higher X-ray doses towards the patient. These X-ray doses are harmful for the patient. Additionally, there is uncertainty regarding the calculated 3D coordinates of the medical instrument.

Document U.S. Pat. No. 6,389,104 describes a medical imaging system allowing the display of a 3D illustration of a medical instrument in its current position and the patient's vascular system. The imaging system comprises processing means able to determine the current position of the medical instrument using a single 2D image acquired by acquisition means.

One drawback with this type of method is that it cannot be applied to the determination of the 3D position of a medical instrument being navigated inside a cavity (the heart for example).

This type of method effectively can only be applied to determining the position of the tip of the medical instrument inside vessels (a vein for example) for the following reason:

A cavity has a larger volume than a vessel.

The number of potential 3D positions of the tip of a medical instrument moved inside a cavity is therefore much higher than the number of potential 3D positions of the tip of a medical instrument being moved inside a vessel.

Methods of the type described in U.S. Pat. No. 6,389,104 cannot therefore be applied to the determination of the current 3D position of the tip of a medical instrument being guided inside a cavity on account of the fact that the number of potential 3D positions therein is too high.

Further, there is no accurate mathematical method allowing calculation of the 3D coordinates of a point using a single 2D image. Therefore, the displayed 3D representation does not represent the medical instrument in its true current position. The displayed 3D representation represents the instrument in its most probable current position. However, the operator does not have any visual information specifying the probability of the accuracy of the displayed current position.

This may lead to degradation of the patient's inner structures by the operator relying on inaccurate data for navigation of the medical instrument.

An aim of the present invention is to propose a medical imaging method and system with which to overcome at least one of the above-mentioned drawbacks.

More precisely, one purpose of the present invention is to propose a medical imaging method and system allowing the accurate tracking of the 3D position of a mobile, guidable medical instrument being navigated within a cavity.

BRIEF SUMMARY OF THE INVENTION

To this end, the invention proposes a method to track the navigation of a mobile, guidable medical instrument, whose movement can be controlled by control means able to provide data on the force applied to the medical instrument to control guiding thereof, as part of a medical imaging method, wherein the method comprises the steps of:

- the acquisition (100) by an acquisition device (2) of at least one 2D image of a cavity for which a 3D representation is available,
- the reception (120) of at least one strain information relative to the force applied to the instrument to control the guiding of said instrument,
- the combination (200, 300) of the strain information, the 2D image and the 3D representation to determine the position of the instrument.

The medical instrument may be a catheter, an endoscope or any other instrument known to persons skilled in the art. Preferably, the 2D image acquired by the acquisition device is a fluoroscopic X-ray image.

Therefore, one solution to the aim of the invention is to use an instrument controlled by control means able to provide a strain information on the force applied to the instrument to command guiding thereof, and to combine this data called strain information data with the 3D representation and the 2D image to determine the current 3D position of the tip of the medical instrument.

By combining data on controlling of the medical instrument for guiding thereof, data on the 2D image and data on the 3D representation, it is possible to determine with accuracy the three-dimensional current position of the medical instrument.

Preferred, but non-limiting aspects, of the method according to the invention are the following:

The data combining step comprises:
- adjustment of the 3D representation over the 2D image to determine the 2D coordinates of the medical instrument with respect to the 3D representation, and
- taking into consideration data on applied force to determine the third coordinate of the instrument with respect to the 3D representation, the method comprises the receiving of data on the previous 3D position of the instrument, said data on the previous 3D position of the instrument being combined with data on applied force to determine the position of the instrument when no information is received indicating that the tip of the medical instrument is in contact with a wall of the cavity, the method further comprises the taking into account of the patient's cardiac cycle and display of the position of the instrument on the 2D view of the 3D representation at each cardiac cycle.

The invention also concerns a medical imaging system comprising:

an acquisition device consisting of a radiation source and a 2D image acquisition sensor for the acquisition of a 2D image of a cavity of a patient, at least one memory, to store at least one 3D representation of the patient's cavity, a guidable medical instrument intended to be moved within a patient's body, the guiding of said instrument being controlled by data on the force applied to the instrument by the user using the control means, a processing unit capable of combining the information derived from data on applied force, data on the 2D image and data on the 3D representation to determine the 3D coordinates of the instrument.

Preferred, but non-limiting, aspects of the system according to the invention are the following:

the system further comprises means to determine that the tip of the medical instrument is in contact with a wall of the cavity inside which the medical instrument is being moved, the processing unit is capable of:

adjusting the 3D image on the 2D image to determine the 2D coordinates of the medical instrument with respect to the 3D representation, and taking into account the data on applied force to determine the third coordinate of the instrument with respect to the 3D representation, the processing unit is capable of receiving data on the previous 3D position of the instrument, said data on the previous 3D position of the instrument being combined with data on applied force to determine the position of the instrument when no information is received indicating that the tip of the medical instrument is in contact with a wall of the cavity.

The invention also concerns a computer program product comprising program code instructions to implement the above-described method.

BRIEF DESCRIPTION OF THE DRAWINGS

Other characteristics and advantages of the invention will become further apparent from the following description, which is given solely for illustration purposes and is non-limiting, and is to be read with reference to the appended drawings in which.

DETAILED DESCRIPTION OF THE INVENTION

The medical imaging method and system of the invention will now be described in more detail with reference to electrophysiological procedure. Evidently, the invention can be applied to other types of interventional procedures.

Guidable Medical Instrument

During electrophysiology procedure, an operator places the distal end—called the working tip—of a guidable medical instrument into a region to be treated inside a patient's body, for example by passing through the blood vessels (veins and arteries) of the patient's vascular system.

The guidable medical instrument may be a (steering) guidable catheter such as a guidable electrophysiology catheter.

The guidable catheter includes control means to apply a force to the end of the catheter. This allows the guiding of the working tip of the guidable catheter. The control means of the guidable catheter are capable of providing data to processing means indicating the force applied to the tip of the catheter to control its guiding.

The guidable catheter may, for example, be of mechanical or magnetic type.

Imaging System

To facilitate the positioning of the working tip of the instrument at the region to be treated, a medical imaging system is used allowing the determination and display of the current position of the medical instrument in the patient.

This imaging system allows the current 3D position of certain points of the medical instrument to be displayed, for example the points forming the working tip of the medical instrument.

In the remainder hereof, it will be considered that it is sought only to display the current 3D position of the working tip of the instrument used by the user during interventional radiology procedure.

Figure 1:
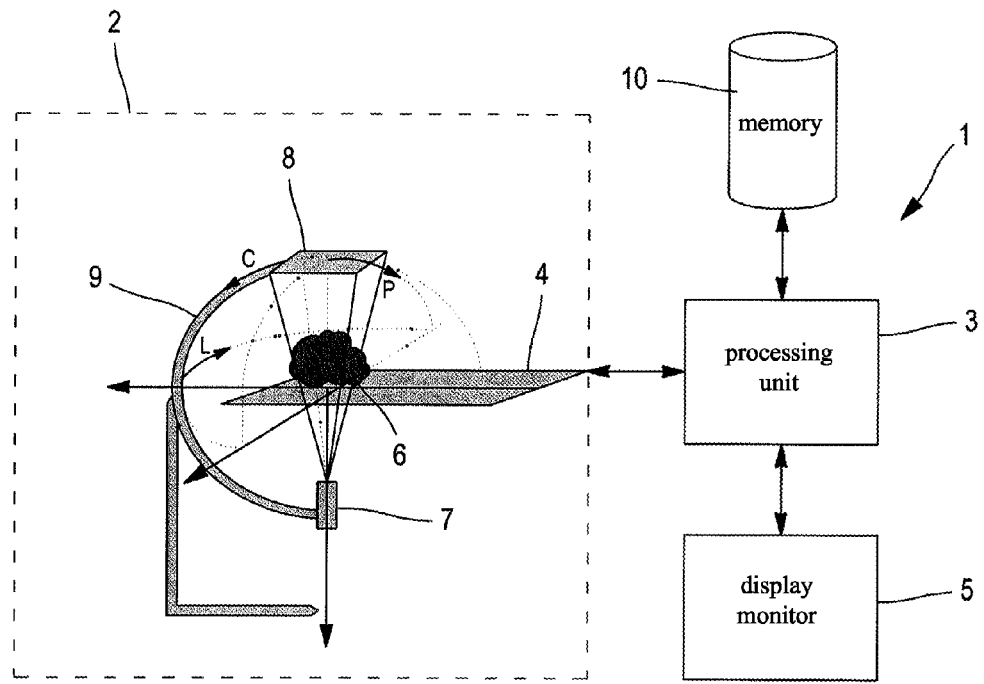
FIG. 1 illustrates one embodiment of the imaging system according to the invention.

With reference to FIG. 1, one embodiment of the imaging system is illustrated. The system comprises an image acquisition device 2, an image processing unit 3 and image display monitor 5.

The acquisition device 2 is used to acquire a 2D image representing the medical instrument and the region to be treated in the patient. The acquisition device comprises a C-arm 9 which, at one of its ends, carries a radiation source 7 and at its other end carries a sensor 8.

The processing unit 3 is capable of implementing the processing methods such as the method described below. The image processing unit 3 may be integrated in the image acquisition system 2, or it may be separate from the image acquisition system 2. The processing unit 3 may for example be one or more computers, one or more processors, one or more microcontrollers, one or more micro-computers, one or more programmable logic controllers, one or more specific application integrated circuits, other programmable circuits, or other devices which include a computer such as a work station.

In one embodiment, the processing unit 3 includes a reading device (not shown) e.g. a disk reader or CD-ROM reader to read the instructions of the medical imaging method (which will be described below) on an instruction medium (not shown) such as a floppy disk or CD-ROM. In another embodiment, the processing unit 3 carries out the instructions of the medical imaging method (which is described below) stored on micro-software (not shown).

The processing unit 3 is coupled to one or more memories 10 which may be integrated in or separate from the processing unit 3. This memory 10 is used in particular to store the 3D representation of the region to be treated in the patient. The memory 10 may be a ROM/RAM memory of the processing unit 3, a CD-ROM, a USB key, a server memory.

The display monitor 5 allows display of the output image illustrating the current 3D position of the instrument. This current 3D position may be superimposed over a 2D view of the 3D representation of the region to be treated in the patient.

The image display monitor 5 may be integrated in the acquisition system 2 or the processing unit 3, or it may be separate from the acquisition device 2 and the processing unit 3. The display monitor 5 may, for example, be a computer monitor, a monitor, a flat panel display, a plasma display or any other type of display known to persons skilled in the art.

Operating Principle

The operating principle of the system in FIG. 1 is as follows.

During electrophysiology procedure, the operator moves the medical instrument 11 inside the body of the patient 6, and uses the instrument's control means to guide the distal end thereof.

As is conventional, the C-arm 9 is able to be pivoted about the axis of a table 4 intended to receive the patient 6 to be imaged, and to be moved relative to this table 4 along various directions schematized by the double arrows in the figure, so as to allow adjustment of the positioning of said C-arm 9 with respect to the part of the patient 6 it is desired to image.

Once the C-arm 9 is in position, the source 7 projects cone-shaped radiation which is received by the sensor 8 after it has passed through the patient 6 to be imaged. The sensor 8 is of matrix type and for this purpose comprises a matrix of detectors.

The processing unit 3 receives, processes, and optionally memorizes the digital 2D images thus obtained in the memory 10. The processing unit 3 is capable of implementing different imaging methods.

In particular, the processing unit 3 is able to implement the medical imaging method described in the remainder hereof. The processing unit 3 notably combines the data derived from the imaging device 2 (2D image), from the memory 10 (3D representation) and the control means (data on applied force) to determine the current 3D position of the tip of the instrument 11.

An output image illustrating the 3D position of the instrument in one or more 2D views of the 3D representation, or directly on the 3D representation, can then be displayed on the display monitor.

Every N seconds, N being a given time interval (for example N=10 milliseconds), the acquisition system acquires projection data to obtain a 2D image. Each 2D image corresponds to a new, current position of the tip of the instrument. The current point position of the tip is determined in real time.

The output image representing the current 3D position of the tip of the instrument can be regenerated every N seconds.

Advantageously, the processing unit is able to take into account the patient's cardiac cycle so as to display a single output image per cardiac cycle.

Medical Imaging Method

A more detailed description will now be given of the method according to the invention, for the navigation of a guidable medical instrument intended to be moved inside a patient's body.

With this method, it is possible in particular to obtain an output image representing the current 3D position of the working tip of the instrument.

The method comprises the following steps:
- the receiving 100 of at least one 2D image of an observation region in a patient, acquired by an acquisition device,
- the receiving 110 of a 3D representation of the observation region,
- the receiving 120 of at least one data item on the force applied to the instrument to control the guiding of said instrument inside the patient's body.

On the basis of these data derived from information on applied force, the 2D image and the 3D representation of the cavity, the method comprises a determination step 200, 300 to determine the position of the instrument inside the patient's body.

These different steps will now be described in further detail.

Receiving of the 2D Image

As recalled above, one of the steps of the method consists of receiving 100 a 2D image acquired during the guiding of the medical instrument inside the patient. This 2D image is a fluoroscopic 2D image for example, acquired by the above-described imaging system.

Processing is conducted on this 2D image to locate the position of the instrument in the 2D image. To locate the instrument in the 2D image, all methods known to those skilled in the art can be used. These methods may comprise morpho-mathematical pre-processing (expansion, erosion and their combination as open and close operations), thresholding to obtain a binary image, and post-processing to smooth the image, etc.

Receiving of the 3D Representation

Another step of the method consists of receiving 110 the 3D representation of the patient region to be treated.

To obtain the 3D representation, any methods known to persons skilled in the art can be used, for example the method described in document U.S. Pat. No. 6,389,104. It is also possible to obtain the 3D model of the patient using a scanning method allowing the acquisition of slice images of a portion of the patient's body (for example the patient's torso).

Adjustment Between the 3D Representation and the 2D Image

The 3D representation and the 2D image are then adjusted so as to superimpose the 2D image over a 2D view of the 3D representation.

The adjustment step can be conducted manually or automatically.

To adjust the 3D representation and the 2D image, methods known to persons skilled in the art can be used. For example, adjustment may make use of the patient's inner structures or external markers, or any other method known to those skilled in the art.

The adjustment between the 3D representation and the 2D image allows determination of two of the three coordinates defining the current 3D position of the tip of the instrument seen in the 2D image (coordinates X and Y).

The position and orientation of the patient, at the time the fluoroscopic 2D image is acquired, then correspond to the position and orientation of the 3D representation which allowed the 2D view of the 3D representation to be obtained, which is superimposed over the acquired fluoroscopic 2D image.

The reader will have appreciated that there is uncertainty regarding adjustment owing to mechanical inaccuracies, any patient movement when the fluoroscopic 2D image is acquired, or attributable to any deformation of the tip of the instrument.

Receiving Data on Applied Force

A further step of the method consists of receiving 130 information on the force applied to the instrument to control the guiding of said instrument inside the patient's body.

Figure 3:
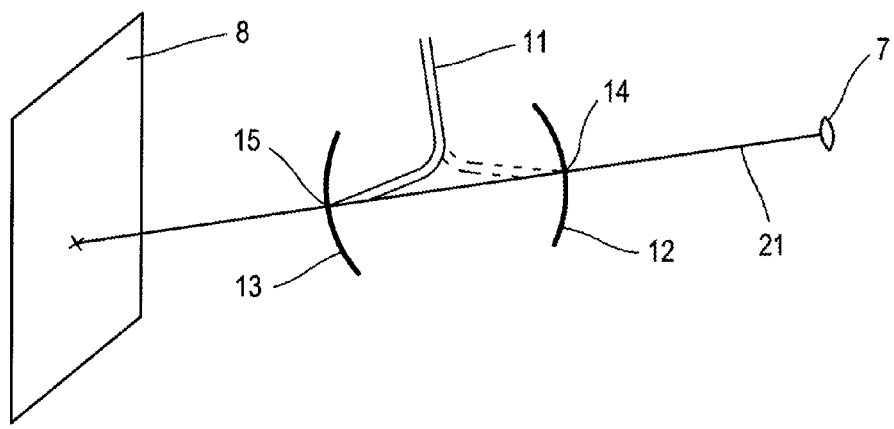
FIG. 3 illustrates the potential positions of a distal end of a guidable medical instrument relative to a source, and a sensor of the imaging system according to the invention.
Figure 2:
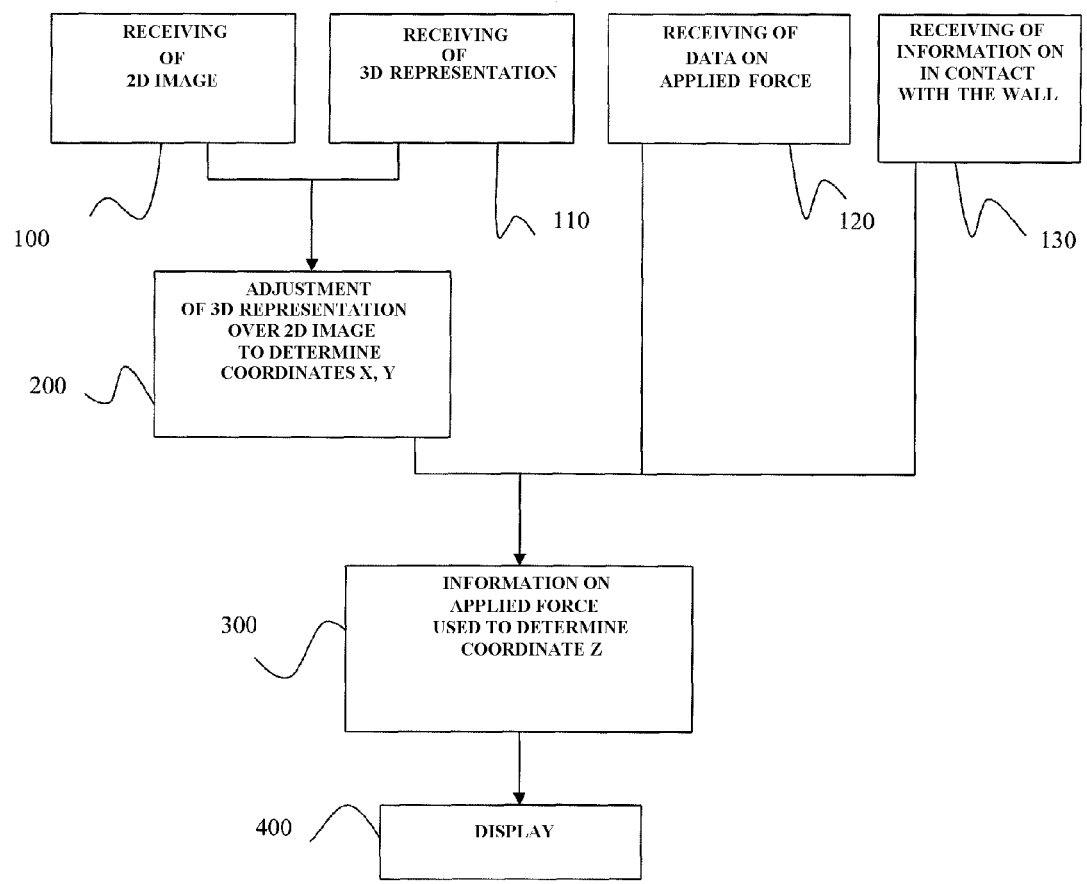
FIG. 2 illustrates an embodiment of the medical imaging method according to the invention.

As illustrated in FIG. 3, once adjustment between the 3D representation and the 2D image has been made (superimposition 200 of the 2D image and the 2D view of the 3D representation) it is known that the tip of the instrument 11 lies somewhere on an axis 21 leading from the X-ray source 7 to the sensor 8.

The information contained in the fluoroscopic 2D image being insufficient to determine the 3D coordinates of the tip of the instrument, use is therefore made of:

- conditions regarding position, which must be verified by the tip of the instrument, and
- information on the force applied to the instrument to control the guiding of the tip of said instrument inside the patient's body.

During electrophysiological procedure, the operator places the distal end of the instrument 11 in contact with the wall 12, 13 of the body organ to be treated.

Advantageously, the method may comprise a step 130 to receive information indicating that the tip of the medical instrument is in contact with a wall of the cavity in which the medical instrument is being navigated.

Knowledge of the fact that the tip of the medical instrument is in contact with a wall of the cavity can be obtained using numerous means, for example:

- measurement of impedance (the impedance of the medical instrument differs according to whether or not the tip of the instrument is in contact with the wall),
- measurement of electric signals (the electric signals of the medical instrument vary according to whether or not its tip is in contact with the wall),
- examination of the movement of the tip of the medical instrument (if the cavity is the heart, the movement of the tip of the medical instrument differs according to whether or not it is in contact with a wall of the cavity).

Evidently, other methods known to persons skilled in the art can be used to determine whether or not the tip of the medical instrument is in contact with a wall of the cavity.

Therefore this condition regarding the position of the tip of the instrument 11 reduces to two the number of potential positions 14, 15 of the distal end of the instrument 11 on the axis 21 leading from the source 7 to the sensor 8: the distal end of the instrument 11 is in contact either with the wall 12 of the body organ lying closest to the source 7, or with the wall 13 of the body organ lying furthest from the source 7.

For each new 2D image acquired, consideration is given to an axis 21 joining together the X-ray emission means 7 with projection of a point of the tip onto the X-ray image taking means 8. This axis is used to define coordinate Z (Z axis) of an orthonormal reference having an abscissa X and ordinate Y.

Taking into consideration the information on the force applied to the instrument to control guiding of its distal end, it is determined whether the force applied to the instrument tends to direct the distal end of the instrument towards the wall of the body organ the closest to the source, or towards the wall of the body organ furthest from the source.

This allows the number of potential positions of the distal end of the instrument on the axis 21 to be reduced to a single position, which corresponds to the current position of the tip of the medical instrument.

With the imaging method, it is therefore possible to manage the ambiguities regarding the 3D position of the tip of the instrument, and thereby to display the current 3D position of the tip of the instrument with accuracy.

As a variant, information on the previous 3D position of the working tip of the medical instrument is used, to determine the current 3D position thereof. The current position of the tip of the instrument relates to its previous position: the movement of the tip of the medical instrument is continuous, which means that if the acquisition of a 2D image at time t is close in time to the acquisition of a 2D image at time t−1, then the 3D position of the tip of the instrument at time t will be spatially close to the 3D position of the tip of the instrument at time t−1.

However, in this variant of the invention, the determination of the current 3D position of the tip of the instrument is less precise than in the embodiment comprising a step to receive information indicating that the tip of the medical instrument is in contact with a wall of the cavity.

Display of the Result

The described method allows the current point 3D position of the tip of the instrument to be determined from a 2D image.

The result can be displayed in the form of a 2D view of the 3D representation with volume representation.

Advantageously, the operator can select different viewpoints for display of the 2D view, using the data entry means of the imaging system, for example a mouse or keyboard (touch screen, etc.).

As a variant, the 3D representation can be rotated automatically or manually for better comprehension of the 3D position of the tip of the medical instrument.

Another form of display may be as follows. As seen previously, the 2D image is acquired by the acquisition device 2 from one viewpoint. The processing unit 3 is capable of determining a 2D view from the same viewpoint as the viewpoint for the 2D image, and of determining a 2D view from a viewpoint opposite to the viewpoint from which the 2D image was acquired. The data entry means of the system then allow selection either of the 2D view of the 3D representation as determined from the same viewpoint as the viewpoint used for acquisition of the 2D image, or the 2D view of the 3D representation as determined from an opposite viewpoint to the viewpoint used for acquisition of the 2D image. The selected 2D view is then displayed on the display monitor 5.

The above-described medical imaging method and assembly can facilitate the positioning of the working tip of the instrument in the region to be treated.

They also allow determination of the current 3D position of one or more points of the instrument.

The reader will appreciate that numerous modifications may be made hereto, without departing in substance from the novel teaching and advantages described herein.

For example, in the different embodiments described above, the acquisition system is an X-ray image acquisition system. However, the acquisition system may be of any other type. For example, the image acquisition system 2 may be an ultrasound image acquisition system, a magnetic resonance image acquisition system (MRI), an image acquisition system using single photon emission computed tomography (SPECT), an image acquisition system using computed tomodensitometry (CT), an image acquisition system using positron emission tomography (PET).

Therefore, any modifications of this type are intended to be incorporated within the scope of the imaging system and method such as defined in the appended claims.

REFERENCES 1 medical imaging system
2 acquisition device
3 processing unit
4 table
5 display monitor
6 patient
7 source
8 sensor
9 C-arm
10 memory
11 medical instrument
12, 13 walls of body organ
14, 15 potential positions of the tip of the instrument 100 acquiring
110 receiving of 3D representation
120 receiving of strain information
130 receiving of data indicating that the instrument is in contact with a wall of the cavity
200 adjusting of 3D representation over 2D image
300 taking into account of the strain information
400 display

What is claimed is:

1. A method to monitor the navigation of a mobile, guidable, medical instrument as part of a medical imaging method, the method comprising:
   acquiring, by an acquisition device comprising a radiation source and a sensor, at least one 2D image of a cavity for which a 3D representation is available and acquiring, the 3D representation;
   receiving information indicating that a tip of the medical instrument is in contact with a first wall of the cavity in which the medical instrument is being navigated;
   for each of the at least one 2D image, defining an axis joining together the radiation source of the acquisition device and a projection point of the medical instrument tip onto the sensor of the acquisition device;
   receiving data indicative of at least one strain information relative to a force applied to the medical instrument to control guiding of the medical instrument to determine a point corresponding to a wall of the cavity that is closest to the radiation source of the acquisition device and a point corresponding to a wall of the cavity that is furthest from the radiation source of the acquisition device;
   based on the at least one strain information and when the medical instrument tip is in contact with the first wall of the cavity, determining whether the force applied to the medical instrument tends to direct the medical instrument tip towards the wall of the cavity closest to the radiation source of the acquisition device or towards the wall of the cavity furthest from the radiation source of the acquisition device; and
   combining the at least one strain information, the at least one 2D image and the 3D representation to determine a position of the medical instrument.

2. The method of claim 1, wherein combining the at least one strain information, the at least one 2D image and the 3D representation to determine the position of the medical instrument further comprises:
   adjusting the 3D representation over the at least one 2D image to determine 2D coordinates of the medical instrument relative to the 3D representation; and
   processing the at least one strain information to determine a third coordinate of the medical instrument relative to the 3D representation.

3. The method of claim 1, further comprising:
   receiving data indicative of a patient's cardiac cycle and displaying the position of the medical instrument in a 2D view of the 3D representation at each of the patient's cardiac cycle.

4. A medical imaging system, comprising:
   an acquisition device comprising a radiation source and a 2D image acquisition sensor for acquiring at least one 2D image and for acquiring a 3D representation of a cavity;
   at least one memory configured to store the 3D representation of the cavity;
   a mobile, guidable, medical instrument; and
   a processing unit configured to:
      determine that a tip of the medical instrument is in contact with a first wall of the cavity in which the medical instrument is being navigated;
      define an axis joining together the radiation source of the acquisition device and a projection point of the medical instrument tip onto the 2D image acquisition sensor of the acquisition device for each of the at least one 2D image;
      receive data indicative of at least one strain information relative to a force applied to the medical instrument to control guiding of the medical instrument to determine a point corresponding to a wall of the cavity that is closest to the radiation source of the acquisition device and a point corresponding to a wall of the cavity that is furthest from the radiation source of the acquisition device;
      based on the at least one strain information and when the medical instrument tip is in contact with the first wall of the cavity, determine whether the three applied to the medical instrument tends to direct the medical instrument tip towards the wall of the cavity closest to the radiation source of the acquisition device or towards the wall of the cavity furthest from the radiation source of the acquisition device; and
      combine the at least one strain information, the at least one 2D image and the 3D representation to determine 3D coordinates of the medical instrument.

5. The system of claim 4, wherein the processing unit is further configured to:
   adjust the 3D representation over the at least one 2D image to determine 2D coordinates of the medical instrument with respect to the 3D representation; and
   process the at least one strain information to determine a third coordinate of the medical instrument relative to the 3D representation.

6. A non-transitory computer readable medium comprising program code instructions configured to implement the method of claim 1 when said program is executed on a computer.

* * * * *

UNITED STATES PATENT AND TRADEMARK OFFICE
CERTIFICATE OF CORRECTION

PATENT NO. : 8,467,850 B2
APPLICATION NO. : 12/754693
DATED : June 18, 2013
INVENTOR(S) : Soubelet et al.

It is certified that error appears in the above-identified patent and that said Letters Patent is hereby corrected as shown below:

In the Claims:

In Column 10, Line 32, in Claim 4, delete "three" and insert -- force --, therefor.

Signed and Sealed this
Thirteenth Day of August, 2013

Teresa Stanek Rea
*Acting Director of the United States Patent and Trademark Office*